(12) United States Patent
Jiang et al.

(10) Patent No.: US 9,006,419 B2
(45) Date of Patent: Apr. 14, 2015

(54) METHOD FOR ISOLATING NUCLEIC ACIDS

(75) Inventors: Pei-Shin Jiang, Taichung (TW); Kun-Chan Wu, Yuanli Township (TW); Yu-Ting Su, Zhudong Township (TW); Chia-Yun Lin, Taipei (TW); Siou-Cing Su, Kaohsiung (TW); Yuh-Jiuan Lin, Taishan Township (TW)

(73) Assignee: Industrial Technology Research Institute, Hsinchu (TW)

( * ) Notice: Subject to any disclaimer, the term of this patent is extended or adjusted under 35 U.S.C. 154(b) by 1154 days.

(21) Appl. No.: 12/905,777

(22) Filed: Oct. 15, 2010

(65) Prior Publication Data

US 2011/0097782 A1   Apr. 28, 2011

(30) Foreign Application Priority Data

Oct. 22, 2009   (TW) ............................... 98135732 A

(51) Int. Cl.
  *C12N 1/08* (2006.01)
  *C12N 15/10* (2006.01)
(52) U.S. Cl.
  CPC ................................. *C12N 15/1006* (2013.01)
(58) Field of Classification Search
  USPC ....................................................... 536/25.4
  See application file for complete search history.

(56) References Cited

U.S. PATENT DOCUMENTS

| | | | |
|---|---|---|---|
| 5,428,146 A * | 6/1995 | Logemann et al. ........ 800/317.2 |
| 5,646,263 A | 7/1997 | Ekenberg et al. |
| 5,693,784 A | 12/1997 | Ekenberg |
| 5,705,628 A | 1/1998 | Hawkins |
| 5,898,071 A | 4/1999 | Hawkins |
| 5,945,525 A | 8/1999 | Uematsu et al. |
| 6,027,945 A | 2/2000 | Smith et al. |
| 6,255,477 B1 | 7/2001 | Kleiber et al. |
| 6,274,386 B1 | 8/2001 | Harttig |
| 6,368,800 B1 | 4/2002 | Smith et al. |
| 6,562,568 B1 | 5/2003 | Kleiber et al. |
| 6,582,922 B1 | 6/2003 | Daimon et al. |
| 6,617,105 B1 | 9/2003 | Rudi et al. |
| 6,673,631 B1 | 1/2004 | Tereba et al. |
| 6,718,742 B1 | 4/2004 | Baker |
| 6,787,307 B1 | 9/2004 | Bitner et al. |
| 6,855,499 B1 | 2/2005 | Nargessi |
| 6,914,137 B2 | 7/2005 | Baker |
| 6,936,414 B2 | 8/2005 | Gundling |
| 6,972,329 B2 | 12/2005 | Burgoyne |
| 7,022,835 B1 | 4/2006 | Rauth et al. |
| 7,067,287 B1 | 6/2006 | Sakurai et al. |
| 7,264,927 B2 | 9/2007 | Nargessi et al. |
| 2003/0008320 A1 | 1/2003 | Baker |
| 2003/0054395 A1 | 3/2003 | Baker |
| 2003/0096987 A1 | 5/2003 | Uematsu et al. |
| 2003/0148101 A1 | 8/2003 | Sauer et al. |
| 2003/0199078 A1 | 10/2003 | Kleiber et al. |
| 2004/0072215 A1 | 4/2004 | Rudi et al. |
| 2004/0137449 A1 | 7/2004 | Nargessi |
| 2004/0197780 A1 | 10/2004 | McKernan et al. |
| 2004/0214175 A9 | 10/2004 | McKernan et al. |
| 2005/0021926 A1 | 1/2005 | Liao et al. |
| 2005/0214926 A1 | 9/2005 | Zielenski et al. |
| 2007/0178601 A1* | 8/2007 | McCormick .................. 436/166 |
| 2009/0069554 A1* | 3/2009 | Finne ......................... 536/25.41 |

FOREIGN PATENT DOCUMENTS

| | | |
|---|---|---|
| CN | 1680421 A | 10/2005 |
| CN | 1891833 A | 1/2007 |
| EP | 1388588 A1 | 2/2004 |

OTHER PUBLICATIONS

Chinese Office Action, dated Jun. 19, 2013, for Chinese Application No. 200910217168.7.
Taiwanese Office Action for Taiwanese Application No. 98135732 dated Feb. 6, 2013.

\* cited by examiner

*Primary Examiner* — Kenneth Horlick
(74) *Attorney, Agent, or Firm* — Birch, Stewart, Kolasch & Birch, LLP

(57) ABSTRACT

A method for isolating nucleic acids is provided. The method includes providing a biological sample containing at least one nucleic acid, and mixing the biological sample with an isolating agent under a suitable condition to isolate the nucleic acids from the biological sample in single step, wherein the isolating agent contains 1-40 wt % of PEG and/or more than 30 wt % of low molecular weight alcohol, a salt, and a detergent. Isolated nucleic acids are bound to a solid support by changes in the solubility of nucleic acids. Additionally, the present invention further provides an isolating agent and kit for isolating nucleic acids.

21 Claims, 1 Drawing Sheet

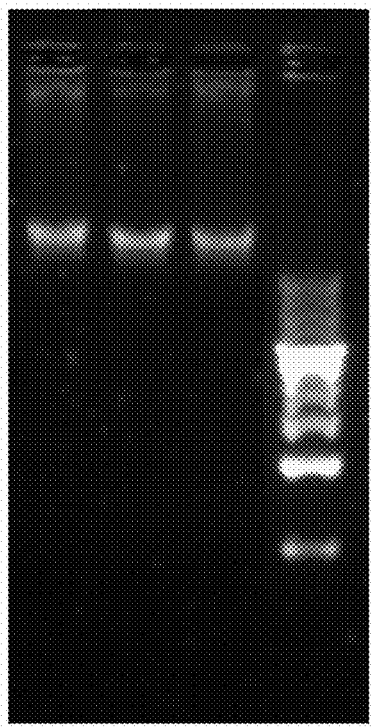

METHOD FOR ISOLATING NUCLEIC ACIDS

CROSS REFERENCE TO RELATED APPLICATIONS

This Application claims priority of Taiwan Patent Application No. 98135732, filed on Oct. 22, 2009, the entirety of which is incorporated by reference herein.

TECHNICAL FIELD

The present invention relates to a method for isolating nucleic acids, and in particular relates to a single-step method for isolating a nucleic acid and an isolating agent.

BACKGROUND

Nucleic acid analysis is being frequently used, due to increased application in molecular diagnosis, pharmacogenomics, medicine, and criminal identification. Conventional nucleic acid analysis methods, strive for convenient and speedy results, wherein the nucleic acids have high purity.

In order to resolve the problems of degradation of nucleic aids and undesired byproducts during the analysis process, various methods have been developed for nucleic acid isolation. In one case, a solid support or a column containing beads is provided to bind the nucleic acids, and then the nucleic acids are eluted from the solid support or beads. For the magnetic beads method, magnetic beads are provided to bind the nucleic acids and then the nucleic acids are obtained by magnetism.

Since the magnetic beads method does not require concentrations or a vacuum process, it has the advantages of being a faster, simpler, more convenient, and lower cost method when compared to other methods. Thus, currently, the magnetic beads method is the most popular method for isolating nucleic acids.

Generally, in the conventional methods, complicated samples are first treated to release nucleic acids and then the nucleic acids are bound to a solid support. For example, U.S. Pat. No. 5,234,809 discloses a method wherein nucleic acids are absorbed by silica materials utilizing chatropic salt. After a washing step, the absorbed nucleic acids are eluted from the silica materials. Meanwhile, U.S. Pat. No. 6,274,386 discloses using a magnetic solid support with a silica surface to absorb nucleic acids.

However, lysis, concentration, precipitation, washing, and elution steps are necessary in all conventional isolation methods. Thus, the conventional methods are time-consuming and easily cause contamination.

Thus, a novel method for isolating nucleic acids is required to simply and quickly isolate nucleic acids.

SUMMARY

The disclosure provides a method for isolating nucleic acids, comprising: mixing an isolating agent and a biological sample containing nucleic acids to isolate the nucleic acids from the biological sample, wherein the isolated nucleic acids are bound to a solid support. The isolating agent comprises 1-40 wt % of PEG and/or more than 30 wt % of low molecular weight alcohol, a salt, and a detergent. The binding of the nucleic acids and the solid support is achieved by changes in the solubility of the nucleic acids.

The disclosure also provides an isolating agent, comprising 1-40 wt % of PEG and/or more than 30 wt % of low molecular weight alcohol, a salt, and a detergent, and a solid support.

The disclosure further provides a kit for isolating nucleic acids, comprising an isolating agent. The isolating agent comprises 1-40 wt % of PEG and/or more than 30 wt % of low molecular weight alcohol, a salt, and a detergent, and a container.

A detailed description is given in the following embodiments with reference to the accompanying drawings.

BRIEF DESCRIPTION OF THE DRAWINGS

The disclosure invention can be more fully understood by reading the subsequent detailed description and examples with references made to the accompanying drawings, wherein:

FIG. 1 is the results of an electrophoresis analysis.

DETAILED DESCRIPTION

The following description is of the best-contemplated mode of carrying out the invention. This description is made for the purpose of illustrating the general principles of the invention and should not be taken in a limiting sense. The scope of the invention is best determined by reference to the appended claims.

The disclosure provides a method for isolating and/or purifying nucleic acids. The method comprises mixing an isolating agent and a biological sample containing nucleic acids to isolate the nucleic acids from the biological sample.

In one embodiment, the isolating agent comprises 1-40 wt % of poly(ethylene glycol) (PEG), preferably, 5-20 wt % of PEG.

In another embodiment, the isolating agent comprises more than 30 wt % of low molecular weight alcohol, preferably 40-60 wt %, wherein the low molecular weight alcohol has a molecular weight of 30-100 g/mol. In one embodiment, the low molecular weight alcohol is ethanol.

In another embodiment, the isolating agent comprises both PEG and low molecular weight alcohol.

The isolating agent further comprises a salt, a detergent, a protease, and/or a solid support.

The term "salt" is used herein to refer to any salt for molecular biology experiments. The salt comprises an alkali metal, an alkaline earth metal, and/or an ammonium salt. For example, $Li^+$, $Na^+$, $K^+$, $Rb^+$, $Cs^+$, $Fr^+$, $Gu^+$ (guanidine), $Be^{2+}$, $Mg^{2+}$, $Ca^{2+}$, $Sr^{2+}$, $Ba^{2+}$, $Ra^{2+}$, and/or $NH_4^+$. In one embodiment, the salt can include a halogen, preferably, $Cl^-$. Generally, the salt of the invention includes, but is not limited to, Gu-HCl (guanidine hydrochloride), LiCl, NaCl, Tris-HCl, Gu-SCN (guanidine thiocyanate), or the like.

The term "detergent" is used herein to refer to an ionic detergent, ampholytic detergent, or nonionic detergent, preferably, ampholytic detergent or nonionic detergent. The nonionic detergent can be a polyoxyethylene nonionic detergent, such as, Tween 20, Triton X-100, NP40, or Brij35. The concentration and amount of the nonionic detergent are not limited. For example, the concentration of the nonionic detergent can be 0.01% to 40%, preferably, 5% to 20%. The ampholytic detergent includes, but is not limited to, CHAPS (3-{(3-cholamidopropyl)dimethylammonio}-propanesulfonate). The concentration and amount of the ampholytic detergent are not limited. For example, the concentration of the ampholytic detergent can be 0.01% to 20%, preferably, 1% to 10%.

The term "protease" is used herein to refer to any material having a hydrolyzing protein function. For example, thermophilic protease, pepsin, trypsin, bromelain, alcalase, protease K, flavorzyme, or esperase, etc., preferably, protease K.

The isolating agent can further include polysaccharides, such as glycogen, starch, oligosaccharides, dextran, cellulose, agarose, chitosan, mucopolysaccharides, or peptidoglycan to increase the binding ability of nucleic acids with solid support to improve the yield and purity of nucleic acids.

The term "biological sample" is used herein to refer to any sample containing nucleic acids. The biological sample of the invention is not limited, and includes any material with nucleic acids, chromosomes, and/or plasmids. In one embodiment, the biological sample of the invention can be a fungus, a virus, a microorganism, a cell, a blood sample, an amniotic fluid, a cerebrospinal fluid, or a tissue sample from skin, muscle, buccal, conjunctival mucosa, placenta, or gastrointestinal tract. It should be noted that the biological sample can directly react with the isolating agent without any pretreatment to isolate the nucleic acids.

The term "nucleic acid" is used herein to refer to a natural or synthetic DNA or RNA. The nucleic acid includes, but is not limited to, single strand DNA, double strand DNA, RNA, LNA, PNA, nucleic acid-protein complex, and/or nucleic acid-saccharide complex.

After an isolating agent and a biological sample mixed, a reaction step is performed under a suitable condition. The reaction temperature can be a room temperature (25° C.) or 50° C. to 80° C., preferably, 60° C. to 70° C. The pH value can be about pH 6 to 9, preferably, pH 7 to 8. The reaction time is about 5 to 30 minutes, preferably, 10 to 20 minutes. The biological sample can be treated with the isolating agent without any pretreatment.

If the biological sample is a cell type sample or whole blood sample, the cell can be destroyed to release the nucleic acids by the isolating agent, and the biological sample does not need a centrifugation, isolation, or hydrolysis process. Additionally, the isolated nucleic acids can be purified by conventional methods. For example, the isolated nucleic acids can be washed with ethanol to increase their purity.

In another embodiment, the isolated nucleic acids can be bound to a solid support, and then eluted. The isolating agent changes the solubility and structure of the nucleic acids to improve the binding between the nucleic acids and the solid support.

The term "solid support" is used herein to refer to a magnetic material, a metal, a metal oxide, a silicide, or a polymer. The surface of the solid support can be modified by chemical bounds. In one embodiment, the surface of the solid support has saccharides (carbohydrate), such as cellulose, nitrocellulose, dextran, or the like. In another embodiment, the surface of the solid support has hydrophobic groups, such as $C_{1-30}$ alkyl or $C_{5-30}$ aryl group. In another embodiment, the surface of the solid support has hydrophilic groups, such as hydroxyl, carbonyl, carboxyl, ester, amino, or sulfonyl etc.

In addition, a washing step and/or eluting step can be performed after the reaction step.

The washing step includes adding a wash solution to the sample and isolating agent mixture to remove salts and proteins therefrom. The wash solution of the invention is not limited, and includes any solution for removing protein, polysaccharides, lipids or lysates on the nucleic acids. Generally, the wash solution contains an alcohol and salt. The alcohol can be ethanol or ethylene glycol, and the salt can be NaCl (less than 3 M) or the like. It is preferred that the amount of the wash solution and the frequency of the washing step are enough to remove impurities (proteins, polysaccharides, lipids, or cell lysates) and do not influence the yield of the nucleic acid production.

After the washing step, an eluting step can be performed. The eluting step includes utilizing an elution solution to elute the nucleic acids from the solid support. The elution solution includes, but is not limited to, water, Tris-EDTA (TE) buffer, Tris-acetate-EDTA (TAE) buffer, Tris-borate-EDTA (TBE) buffer, or the like.

The method of the invention can simply and quickly obtain high quality nucleic acids utilizing a single agent (isolating agent) and single step (reaction step). Particularly, pretreatment is unnecessary before the reaction of the biological sample and isolating agent.

The disclosure further provide an isolating agent comprising 1-40 wt % of PEG and/or more than 30 wt % of low molecular weight alcohol.

The isolating agent further comprises salt, detergent, solid support and/or protease as disclosed above.

The disclosure further provides a kit for isolating nucleic acids. The kit comprise an isolating agent comprising 1-40 wt % of PEG and/or more than 30 wt % of low molecular weight alcohol, a salt, and a detergent, a container, and a instruction.

EXAMPLE

Example 1

Nucleic Acid Isolation from Whole Blood

Various isolating agents were used in this example. The isolating agent contained various concentrations of PEG (0%, 5%, 10%, 15%, 20%, or 30%), 3M Gu-HCl, 5% Tween-20, 0.5 µg of magnetic carrier, protease, and 6 M urea.

720 µl of the isolating agent was directly mixed with 200 µl of human whole blood at 56° C. for 10 minutes, wherein the nucleic acids were released from blood cells and bound to the magnetic carrier. The magnetic carrier was then washed by a wash solution (70% EtOH). The nucleic acids absorbed on the magnetic carrier were eluted by 200 µl of DI water for 10 minutes to obtain the nucleic acids.

As shown in Table 1, the DNA of the erythrocyte in the whole blood was directly isolated without pretreatment. About 1-3 µg of DNA was isolated from 200 µl of human whole blood by the above method, and purity ($A_{260}/A_{280}$) was about 1.3-1.6.

TABLE 1

Results of DNA isolation

| PEG concentration (%) | DNA yield (µg) | DNA purity ($A_{260}/A_{280}$) |
| --- | --- | --- |
| 0 | 0.73 | 1.31 |
| 5 | 1.68 | 1.55 |
| 10 | 3.21 | 1.62 |
| 15 | 2.85 | 1.46 |
| 20 | 2.12 | 1.35 |
| 30 | 1.03 | 1.26 |

In another example, PEG, used in the method, was changed to ethanol. The isolating agent contained various concentrations of ethanol (40%, 50%, or 60%), 3M Gu-HCl, 5% Tween-20, 0.5 µg of magnetic carrier, protease, and 6 M urea. The washing buffer was 70% EtOH. About 2 µg of DNA was isolated from 200 µl of human whole blood by the above method, and purity ($A_{260}/A_{280}$) was about 1.3-1.6.

Example 2

Nucleic Acid Isolation from Whole Blood or Plasma

In this example, the isolating agent contained 10% PEG, 6M Gu-HCl, 10% Tween-20, 0.5 µg of magnetic carrier, protease, and 6 M urea.

720 μl of the isolating agent was directly mixed with 200 μl of human whole blood or plasma at 56° C. for 10-15 minutes, wherein the nucleic acids were released from blood cells and bound to the magnetic carrier. The magnetic carrier then was washed by a wash solution (70% EtOH), and the nucleic acids absorbed on the magnetic carrier were eluted by 200 μl of DI water for 10 minutes to obtain the nucleic acids.

In this example, the MegaZorb® kit (Promega) was used as a positive control (conventional method for isolating nucleic acids). The method of the MegaZorb® includes lysis, concentration, precipitation, washing, and elution steps. The yield and purity of isolated nucleic acids were determined as shown in Table 2. About 5 μg of DNA was isolated from 200 μl of human whole blood by the above method, and purity ($A_{260}/A_{280}$) was about 1.89. The isolating agent was directly treated with complicated samples, such as whole blood without pretreatment to isolate the nucleic acids.

TABLE 2

Results of DNA isolation

| | Sample type | Yield of DNA (μg) | Purity of DNA ($A_{260}/A_{280}$) |
|---|---|---|---|
| MegaZorb ®'s method | Whole blood | 2.25 ± 0.86 | 1.58 ± 0.12 |
| | Plasma | 5.38 ± 0.2 | 1.18 ± 0.07 |
| Method of the invention | Whole blood | 4.5 ± 0.3 | 1.89 ± 0.07 |
| | Plasma | 5.13 ± 0.21 | 1.89 ± 0.09 |

In another example, the same method and isolating agent were used to isolate the nucleic acids from human whole blood. The MegaZorb® kit was used as a positive control. This experiment was repeated 3 times.

As shown in Table 3, the nucleic acids were efficaciously isolated from the whole blood by the isolating agent of the invention, and the isolation results were equal to the commercial product. Note that the purity of the isolated DNA was higher and the repeated error was lower in the method of the invention when compared to the MegaZorb® kit. About 5 μg of DNA was isolated from 200 μl of human whole blood by the above method, and purity ($A_{260}/A_{280}$) was about 1.9±0.051. The isolated nucleic acids were analyzed by a polymerase chain reaction.

TABLE 3

Results of DNA isolation

| | DNA concentration (ng/μl) | DNA purity ($A_{260}/A_{280}$) |
|---|---|---|
| MegaZorb ® | 27.66 | 1.69 |
| MegaZorb ® | 26.34 | 1.82 |
| MegaZorb ® | 27.59 | 1.87 |
| Method of the invention | 25.84 | 1.85 |
| Method of the invention | 25.88 | 1.95 |
| Method of the invention | 23.27 | 1.92 |

In another example, the same method and isolating agent were used to isolate the nucleic acids from human whole blood at room temperature. According to this method, about 4 μg of DNA was isolated from 200 μl of human whole blood, and purity ($A_{260}/A_{280}$) was about 1.7.

Example 3

Nucleic Acids Isolation from Cells

In this example, the isolating agent contained 10% PEG, 6M Gu-HCl, 10% Tween-20, 0.5 μg magnetic carrier, protease, and 6 M urea.

720 μl of the isolating agent was directly mixed with 200 μl of mouse CT26 colon adenocarcinoma cells ($8\times10^5$ cells/ml) at 56° C. for 10 minutes so that the nucleic acids were released from blood cells and bound to the magnetic carrier. The magnetic carrier then was washed by a wash solution (70% EtOH), and results are shown in Table 4. The MegaZorb® kit was used as a positive control.

TABLE 4

Results of DNA isolation

| | DNA concentration (ng/μl) | DNA purity ($A_{260}/A_{280}$) |
|---|---|---|
| MegaZorb ® | 35.7 | 1.9 |
| Method of the invention | 36.75 | 1.84 |
| Method of the invention | 34.5 | 1.84 |

As shown in Table 4, the nucleic acids were directly isolated from the cells by the method and isolating agent of the invention. About 7 μg of DNA was isolated from $10^5$ cells, and purity ($A_{260}/A_{280}$) was above 1.8.

The isolated nucleic acids were analyzed by electrophoresis. In FIG. 1, the nucleic acids isolated by the MegaZorb® were loaded in lane 1 of the electrophoresis image, the nucleic acids isolated by the method of the invention were loaded in lanes 2 and 3, and lane 4 showed a pattern of the 1 kb DNA marker. Referring to FIG. 1, high molecular weight DNA existed in all lanes indicated that the method of the invention could directly isolate nucleic acids from cells, and the isolated nucleic acids had high purity and production yield.

While the disclosure has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for isolating nucleic acid, comprising:
   mixing an isolating agent and a biological sample containing nucleic acids to isolate the nucleic acids from the biological sample without any pretreatment, wherein the isolated nucleic acids are bound to a solid support,
   and the isolating agent comprises 1-40 wt % of PEG and/or more than 30 wt % of low molecular weight alcohol, a salt, and a detergent, and
   the binding of the nucleic acids and the solid support is achieved by changes in the solubility of the nucleic acids.

2. The method as claimed in claim 1, wherein the low molecular weight alcohol has a molecular weight of 30-100 g/mol.

3. The method as claimed in claim 1, wherein the low molecular weight alcohol is ethanol.

4. The method as claimed in claim 1, wherein the low molecular weight alcohol has a concentration of 40-60 wt %.

5. The method as claimed in claim 1, wherein the PEG has a concentration of 5-20 wt %.

6. The method as claimed in claim 1, wherein the solid support comprises a magnetic material, a metal, a metal oxide, a silicide, or a polymer.

7. The method as claimed in claim 1, wherein the salt comprises an alkali halide, an alkaline earth halide, and/or an ammonium halide.

8. The method as claimed in claim 1, wherein the detergent comprises polyoxyethylene (20) sorbitan monolaurate, polyethylene glycol p-(1,1,3,3-tetramethylbutyl)-phenyl ether, nonyl phenoxypolyethoxylethanol, polyoxyethylene (23) dodecanol, 3-[(3-cholamidopropyl)dimethylammonio]-1-propanesulfonate.

9. The method as claimed in claim 1, wherein the isolating agent further comprises a protease.

10. The method as claimed in claim 1, wherein the isolating agent further comprises a saccharide.

11. The method as claimed in claim 10, wherein the saccharide comprises a monosaccharide or polysaccharide derivative.

12. The method as claimed in claim 11, wherein the saccharide comprises a glycogen, a starch, a oligosaccharide, a dextran, a cellulose, an agarose, a chitosan, a mucopolysaccharide, or a peptidoglycan.

13. The method as claimed in claim 1, wherein the isolating agent and the biological sample are mixed at a temperature about 50-80° C.

14. The method as claimed in claim 1, wherein the isolating agent and the biological sample are mixed at a temperature about 25° C.

15. The method as claimed in claim 1, wherein the isolating agent and the biological sample are mixed at about pH 6-9.

16. The method as claimed in claim 1, wherein the biological sample contains single strand DNA, double strand DNA, RNA, added LNA, added PNA and/or nucleic acid-protein complex.

17. The method as claimed in claim 1, wherein the biological sample contains cytoplasm.

18. The method as claimed in claim 1, wherein the biological sample comprises a fungus, a virus, a microorganism, a cell, a blood sample, an amniotic fluid, an cerebrospinal fluid, or an tissue sample from skin, muscle, buccal, conjunctival mucosa, placenta, or gastrointestinal tract.

19. The method as claimed in claim 1, further providing a washing step after the biological sample is mixed with the isolating agent.

20. The method as claimed in claim 19, further providing an eluting step after the washing step.

21. The method as claimed in claim 1, wherein the biological sample does not require centrifugation, isolation or hydrolysis prior to isolating the nucleic acids from the biological sample.

* * * * *